(12) United States Patent
Qiu et al.

(10) Patent No.: US 8,232,270 B2
(45) Date of Patent: Jul. 31, 2012

(54) BIVALENT (−)-MEPTAZINOL COMPOUNDS AND/OR THEIR SALTS, AND THEIR PREPARATION AND FUTILIZATION

(76) Inventors: Zhuibai Qiu, Shanghai (CN); Qiong Xie, Shanghai (CN); Hongzhuan Chen, Shanghai (CN); Hao Wang, Shanghai (CN); Zheng Xia, Shanghai (CN); Meiyan Lu, Shanghai (CN); Xinghai Wang, Shanghai (CN)

( * ) Notice: Subject to any disclaimer, the term of this patent is extended or adjusted under 35 U.S.C. 154(b) by 555 days.

(21) Appl. No.: 12/309,580

(22) PCT Filed: Jul. 24, 2007

(86) PCT No.: PCT/CN2007/002243
§ 371 (c)(1),
(2), (4) Date: Sep. 14, 2009

(87) PCT Pub. No.: WO2008/019572
PCT Pub. Date: Feb. 21, 2008

(65) Prior Publication Data
US 2010/0035861 A1    Feb. 11, 2010

(30) Foreign Application Priority Data
Jul. 27, 2006    (CN) .......................... 2006 1 0029477

(51) Int. Cl.
A61P 25/04    (2006.01)
A61P 25/16    (2006.01)
A61P 25/28    (2006.01)
A61K 31/55    (2006.01)
C07D 223/04    (2006.01)
(52) U.S. Cl. .................. 514/217.03; 540/596
(58) Field of Classification Search ............. 514/217.03; 540/596
See application file for complete search history.

(56) References Cited

U.S. PATENT DOCUMENTS
4,021,550 A    5/1977    White et al. ................. 424/244

FOREIGN PATENT DOCUMENTS
| CN | 200410017499.3 | 4/2004 |
| CN | 1569839 A | 1/2005 |
| CN | 200610025390.3 | 3/2006 |
| CN | 1974558 A | 6/2007 |

OTHER PUBLICATIONS

Xie et al, Investigation of the Binding Mode of (−)-Meptazinol and Bis-Meptazinol Derivatives on Acetylcholinesterase Using a Molecular Docking Method, Journal of Molecular Modeling, vol. 12, No. 4, pp. 390-397, Mar. 2006.*

* cited by examiner

*Primary Examiner* — Brenda Coleman

(57) ABSTRACT

The present invention belongs to pharmaceutical field. It relates to a novel family of bivalent (−)-meptazinol compounds and/or their salts, as well as the preparation and utilization of the compounds in the treatment of neurodegenerative disorders and dementias such as Alzheimer's Disease (AD). In the present invention, bivalent (−)-meptazinol compounds were synthesized, from the starting material (−)-meptazinol, successively by N-demethylation forming (−)-normeptazinol and then by acylation with α,ω-alkanediacyl dihalides or alkylation with α,ω-dihaloalkanes. Results from in vitro cholinesterase inhibiting test and AChE-induced Aβ aggregation test demonstrated that the bivalent (−)-meptazinol compounds and/or their salts were novel bivalent inhibitors of both AChE and Aβ aggregation. The most potent compound inhibited both AChE and BChE at nM level, which was 10000 and 1500 times more potent than (−)-MEP hydrochloride, respectively. It inhibited AChE-induced Aβ aggregation by a factor of 2 compared with propidium.

23 Claims, 1 Drawing Sheet

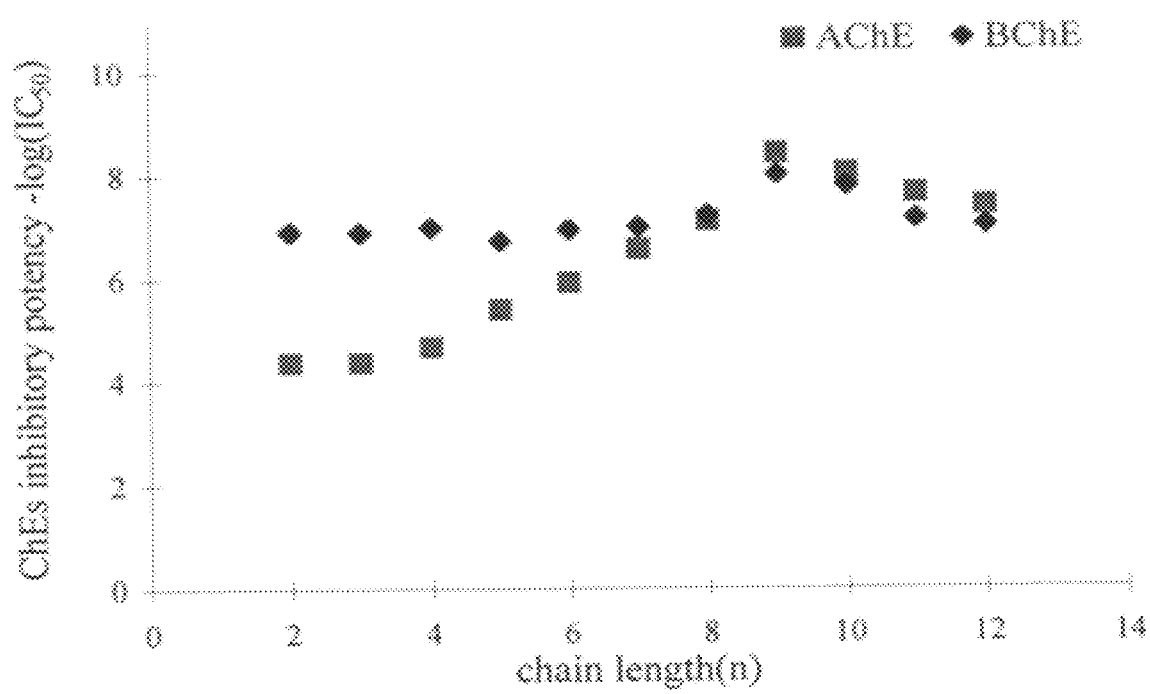

BIVALENT (−)-MEPTAZINOL COMPOUNDS AND/OR THEIR SALTS, AND THEIR PREPARATION AND FUTILIZATION

CROSS REFERENCE TO RELATED APPLICATIONS

The present application claims priority to International Application PCT/CN2007/002243, filed on Jul. 24, 2007, which claims priority to Chinese Patent Application No. 200610029477.8, filed on Jul. 27, 2006. The aforementioned patent applications are hereby incorporated by reference in their entirety.

FIELD OF THE INVENTION

The present invention belongs to pharmaceutical field. It relates to a novel family of bivalent (−)-meptazinol compounds and/or their salts, as well as the preparation and utilization of the compounds referred to. These compounds are useful for the treatment of neurodegenerative disorders like Alzheimer's Disease (AD) and Parkinson's Disease (PD), etc. They are also useful to alleviate cognitive disorders such as senile dementia (such as AD), dementia with Lewy bodies (DLB), and vascular dementia (VaD), etc.

BACKGROUND OF THE INVENTION

Meptazinol (MEP), (±)-3-(3-ethyl-1-methyl-hexahydro-1H-azepin-3-yl)phenol, formula of which is $C_{15}H_{23}NO$, has been marketed for the treatment of moderate to severe pain since 1986. Meptazinol was equivalent to some analgesics like pentazocine, dolantin, and dextromethorphan, and less potent than morphine. Unlike other typical opiates, meptazinol causes much less respiratory depression and lower addictive potential. Therefore, it does not fall within the category of narcotic drugs. Meptazinol is useful for many kinds of acute and chronic pains, such as wound, postoperative, obstetrical and cancer pains. It is especially effective and safe for parturition pain because it does not affect the health of infants. For its safety and reliability, meptazinol was embodied in the British Pharmacopoeia in 1998.

Meptazinol hydrochloride was clinically applied as racemate. Racemic meptazinol can be separated into a pair of enantiomers using optically pure tartaric acid and their derivatives. Enantiomer excess (e.e.) of each enantiomer was authenticated >99% by capillary electrophoresis. The absolute configuration of the levo-enantiomer (−)-MEP was determined to be 3S by X-ray diffraction. By mice brain acetylcholinesterase (AChE) inhibition test, (−)-MEP hydrochloride was verified as potent AChE inhibitor, which indicated that levo-enantiomer of MEP and its salts deserved further research and development.

Progressive loss of memory and impairment in cognition are closely related to the deficit of cholinergic function in basal forebrain and hippocampus. Palliative treatments, targeting elevating brain acetylcholine (ACh) levels and recovering cholinergic nerve conduction, alleviate the memory and cognitive deficits. AChE inhibitors increase the synaptic level of ACh by inhibiting the degradation of ACh.

At present, FDA-approved clinical drugs against AD are mainly AChE inhibitors. They are also used to treat other neurodegenerative disorders like PD and other dementias like DLB and VaD, etc.

Routine AChE inhibitors can only relieve the dementia symptoms, but can not prevent the progression of degenerative pathology. In recent years, it is found that two of the AChE active sites, namely the catalytic triad at the bottom and the peripheral anionic sites (PAS) at the entrance, play a key role in inhibition activity. Many highly potent bivalent and bifunctional AChE inhibitors are designed and synthesized, such as bis-tacrine, bis-huperzine B, etc. More recently, dual binding site AChE inhibitors, which simultaneously block the catalytic site and PAS, were indicated to be involved in dual inhibitory action of both AChE and amyloid-β(Aβ) peptide aggregation. They might not only alleviate the cognitive deficit of AD patients, but also act as disease-modifying agents delaying the progression of degenerative pathology. And there is no report about bivalent meptazinol derivatives both at home and abroad.

SUMMARY OF THE INVENTION

The invention is directed to optically pure bivalent (−)-meptazinol derivatives and/or the pharmaceutically acceptable salts of the referred compounds.

The invention is also directed to the preparation methods of the optically pure bivalent (−)-meptazinol derivatives and/or their pharmaceutically acceptable salts.

The invention is further directed to the high potency of the optically pure bivalent (−)-meptazinol derivatives and/or salts for inhibiting AChE and BChE in vitro, preventing AChE-induced Aβ aggregation. The invention is further directed to the utilization of the optically pure bivalent (−)-meptazinol derivatives and salts in treating neurodegenerative disorders like AD and alleviating the dementia symptom of patients.

Herein bivalent (−)-meptazinol derivatives were designed and synthesized by connecting two (−)-meptazinol unit, based on computer-aided molecular docking approach, in order to simultaneously block both the catalytic and peripheral sites. The correlation between the activity and the alkylene chain length of the bivalent ligands was illuminated as well. The invention aimed at looking for more potent AChE inhibitors with high therapeutic index and low toxicity that could become novel drugs for neurodegenerative disorders and dementias.

The present invention relates to bivalent (−)-meptazinol derivatives represented by the general formula (I):

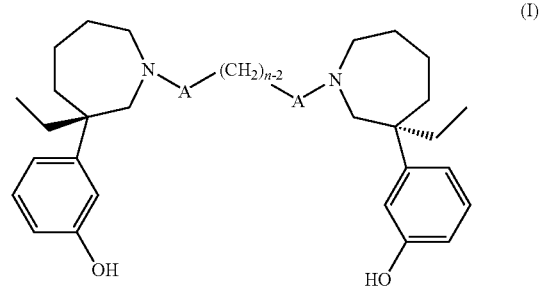

wherein:
A is C═O or $CH_2$,
n is an integer from 2 to 12.

The present invention relates to pharmaceutically acceptable salts of the referred compounds, including pharmaceutically acceptable acid addition salts and pharmaceutically acceptable base addition salts.

BRIEF DESCRIPTION OF DRAWINGS

FIG. 1 illustrates the correlation between mice AChE and BChE inhibitory potency ($-\log IC_{50}$) and the alkylene chain length (n) in the corresponding bivalent (−)-meptazinol compounds ($A=CH_2$, n=2~12).

DETAILED DESCRIPTION OF THE INVENTION

The bivalent (−)-meptazinol derivatives and their salts of the present invention may be prepared in a process routine as described below in Scheme (II):

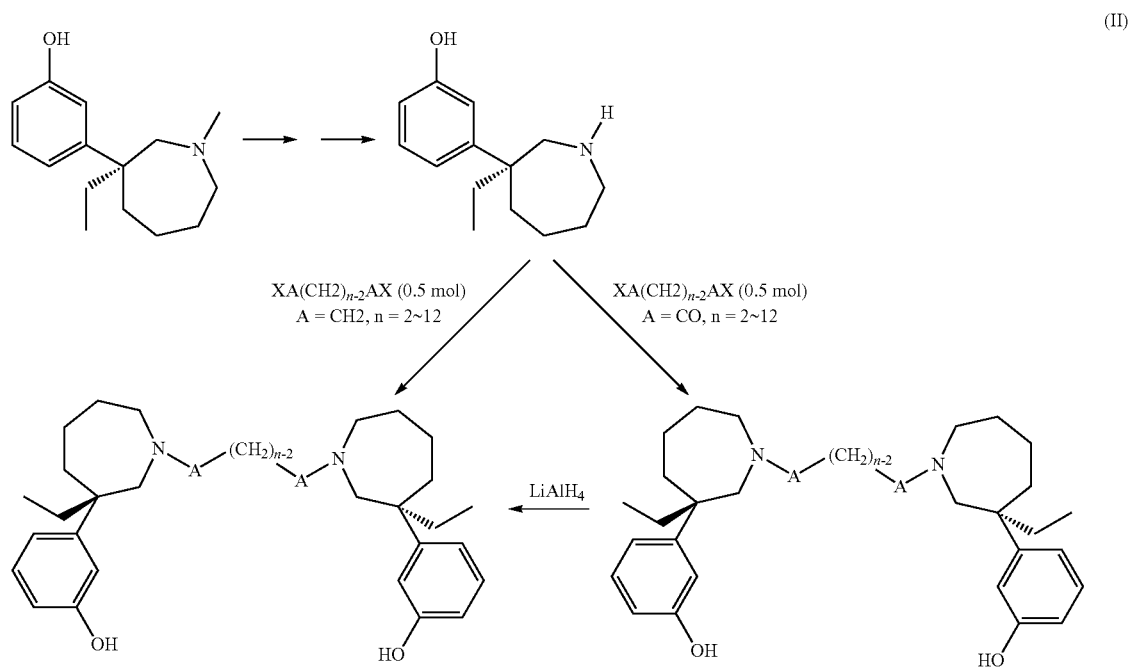

(II)

Follow is a detailed description of each reaction stage in Scheme (II).

1. N-demethylation of (−)-MEP

Treating (−)-MEP with haloformate in a reaction inert solvent, in the presence of a base, afforded an intermediate (−)—N-carboalkoxy-N-demethyl(nor) MEP. Hydrolysis and decarboxylation of the resulting carbamate intermediate produced (−)-nor-MEP.

The reaction is usually carried out in a reaction inert solvent such as tetrahydrofuran (THF), chloroform, methylene chloride, benzene, toluene, N,N-dimethylformamide (DMF), or any mixture of the above solvents. Suitable haloformates for this reaction include ethyl chloroformate, vinyl chloroformate, phenyl chloroformate, and trichloroethyl chloroformate. Suitable bases for this reaction include potassium or sodium bicarbonates. The hydrolysis reaction can be carried out in water solution containing sulfuric acid, or hydrazine hydrate, or THF.

The preferred reaction inert solvent is chloroform. The preferred haloformate is ethyl chloroformate. The preferred base is potassium bicarbonate. And the preferred hydrolysis condition is 50% sulfuric acid solution.

2. Preparation of Bivalent Amide Derivatives of the Formula (I) (Wherein A is C═O and N is an Integer from 2 to 12)

The corresponding bivalent amide derivatives of the formula (I) (wherein A is C═O and n is an integer from 2 to 12) were synthesized by acylation of two (−)-nor-MEPs with α,ω-alkanediacyl dihalide in a reaction inert solvent in the presence of a base.

The reaction inert solvent may be tetrahydrofuran (THF), ether, chloroform, methylene chloride, benzene, toluene, N,N-dimethylformamide (DMF), or any mixture of the above solvents. Suitable bases for this reaction include pyridine, triethylamine, 4-dimethylaminopyridine (DMAP), diisopropylethylamine, potassium or sodium bicarbonates, potassium or sodium hydroxide, etc. Suitable α,ω-diacyl dihalides for this reaction include α,ω-diacyl dichlorides and α,ω-diacyl dibromides.

The preferred reaction inert solvent is methylene chloride. The preferred base is triethylamine. And the preferred α,ω-diacyl dihalides are α,ω-diacyl dichlorides.

3. Preparation of bivalent derivatives of the formula (I) (wherein A is $CH_2$ and n is an integer from 2 to 12)

The corresponding bivalent derivatives of the formula (I) (wherein A is $CH_2$ and n is an integer from 2 to 12) were synthesized by alkylation of two (−)-nor-MEPs with α,ω-dihaloalkanes in a reaction inert solvent in the presence of a base.

The reaction inert solvent may be acetonitrile, tetrahydrofuran (THF), ether, chloroform, methylene chloride, benzene, toluene, N,N-dimethylformamide (DMF), or any mixture of the above solvents. Suitable bases for this reaction include pyridine, triethylamine, 4-dimethylaminopyridine (DMAP), diisopropylethylamine, potassium or sodium bicarbonates, potassium or sodium hydroxide, etc. Suitable α,ω-dihaloalkanes for this reaction include α,ω-dichloroalkanes, α,ω-dibromoalkanes and α,ω-diiodoalkanes, etc.

The preferred reaction inert solvent is acetonitrile. The preferred base is triethylamine. And the preferred α,ω-dihaloalkanes are α,ω-dibromoalkanes.

4. Preparation of Bivalent Derivatives of the Formula (I) (Wherein a is $CH_2$ and N is an Integer from 2 to 12)

An optional preparation of the corresponding bivalent derivatives of the formula (I) (wherein A is $CH_2$ and n is an integer from 2 to 12) is the reduction of bivalent amide derivatives of the formula (I) (wherein A is C=O and n is an integer from 2 to 12) by lithium aluminum hydride (LiAlH$_4$) in dry ether.

Suitable dry solvents are tetrahydrofuran (THF), ether, and dioxane, etc. It is preferably THF.

5. Pharmaceutically Acceptable Salts of the Bivalent (−)-MEP Derivatives (A is CH$_2$, and n is an Integer from 2 to 12)

The corresponding pharmaceutically acceptable salts of the bivalent (−)-MEP derivatives (A is CH$_2$, and n is an integer from 2 to 12) can be salts added to pharmaceutically acceptable inorganic acids or organic acids. Such inorganic acids are hydrochloric acid, hydrobromic acid, hydroiodic acid, sulfuric acid, phosphoric acid, or any mixture of the above acids. Such organic acids are tartaric acid, acetic acid, maleic acid, fumaric acid, benzoic acid, succinic acid, lactic acid, citric acid, gluconic acid, methanesulfonic acid, phenylsulfonic acid, p-toluenesulfonic acid, or any mixture of the above acids.

Examples of the resulting acid addition salts are hydrochloride, hydrobromide, hydroiodide, sulfate or bisulfate, phosphate or biphosphate, tartrate, acetate, malate, fumarate, benzoate, succinate, lactate, citrate, gluconate, methanesulfate, phenylsulfate, p-toluenesulfate, etc.

The corresponding pharmaceutically acceptable salts of the bivalent (−)-MEP derivatives (A is CH$_2$, and n is an integer from 2 to 12) can also be salts added to pharmaceutically acceptable bases. Such bases contain potassium, sodium, lithium, magnesium, calcium, or any mixture of the metal ions.

Examples of the resulting base addition salts are the salts of potassium, sodium, lithium, magnesium, calcium, etc.

Racemic MEP was synthesized following the procedure reported in Chinese Patent No. CN200410017499. And the synthesis of the levo-enantiomer of MEP was carried out according to the route in Chinese Patent No. CN200610025390.3.

The related bivalent (−)-meptazinol compounds and their salts were tested in vitro for the AChE and BChE inhibitory potency.

Method

AChE inhibiting activities were measured by a spectrophotometric assay developed by Ellman et al. It was based on the fact that AChE catalyzes the hydrolysis of acetylcholine, releasing choline and acetic acid. In this assay, acetylthiocholine (AChSC) is hydrolyzed by the enzyme, releasing thiocholine containing a sulfhydrylic group able to react with color indicating reagent. Yellowish products were measured spectrophotometrically, the amount of which reflects the activity of AChE. All the procedures were operated according to the instruction of the AChE reagent kit produced by Nanjing Jiancheng Bio-engineering Institute. Mice brain homogenate prepared in saline was used as a source of AChE; mice serum was the source of BChE.

The AChE activity was determined in a reaction mixture containing 200 μL of a solution of AChE (0.415 U/mL in 0.1 M phosphate buffer, pH 8.0), 300 μL of a solution of 5,5'-dithio-bis(2-nitrobenzoic) acid (3.3 mM DTNB in 0.1 M phosphate buffered solution, pH 7.0, containing NaHCO$_3$ 6 mM), and 30 μL of a solution of the inhibitor (six to seven concentrations). After incubation for 20 min at 37° C., acetylthiocholine iodide (300 μL of 0.05 mM water solution) was added as the substrate, and AChE activity was determined by UV spectrophotometry from the absorbance changes at 412 mm for 3 min at 25° C. The concentration of compound that produced 50% inhibition of the AChE activity (IC$_{50}$) was calculated by nonlinear regression of the response-concentration (log) curve. BChE inhibitory activity determinations were similarly carried out using butyrylthiocholine iodide (0.05 mM) as the substrate. Results are reported as the means ±SEM of IC$_{50}$ obtained from at least three independent measures.

Results of the Inhibitory Tests

The activities of bivalent (−)-meptazinol compound (A=CH$_2$, n=2~12) hydrochlorides for inhibiting AChE and BChE increased compared with the monomer (−)-MEP. When the linker is shorter than 9 carbons, longer linker lengths were related to higher activities. If the linker is longer than 9 carbons, the activities decreased by prolonging the linker length. A linker with 9 carbons is the optimal length in this series. The most potent compound (IC$_{50}$=3.9 nM) showed a 10000-fold and 1400-fold increase, respectively, in inhibiting mice brain AChE, compared with (−)-MEP and rivastigmine. The BChE inhibitory potency was less impacted by chain length. The highest potency (IC$_{50}$=10 nM) was also achieved in the compound with a 9-carbon linker, which was 1500 times and 150 times more potent than (−)-MEP and rivastigmine, respectively. Moreover, its selectivity for AChE was 7 times and 9 times that of (−)-MEP and rivastigmine, respectively.

Table 1 shows the in vitro inhibitory potency for mice brain AChE and mice serum BChE by bivalent (−)-meptazinol compounds (A=CH$_2$, n=2~12).

TABLE 1

| Compounds | linker | IC$_{50}$ (nM) | | AChE |
|---|---|---|---|---|
| bivalent (−)-meptazinols | length (n) | mice brain AChE | mice serum BChE | selectivity |
| (A = CH$_2$, n = 2) | 2 | 43000 ± 20000 | 125 ± 9 | 0.0029 |
| (A = CH$_2$, n = 3) | 3 | 42000 ± 14000 | 132 ± 51 | 0.0031 |
| (A = CH$_2$, n = 4) | 4 | 21400 ± 7600 | 104 ± 29 | 0.0049 |
| (A = CH$_2$, n = 5) | 5 | 4000 ± 1000 | 192 ± 41 | 0.048 |
| (A = CH$_2$, n = 6) | 6 | 1220 ± 20 | 119 ± 20 | 0.098 |
| (A = CH$_2$, n = 7) | 7 | 270 ± 70 | 102 ± 19 | 0.38 |
| (A = CH$_2$, n = 8) | 8 | 79 ± 19 | 63 ± 8 | 0.80 |
| (A = CH$_2$, n = 9) | 9 | 3.9 ± 1.3 | 10 ± 3 | 2.6 |
| (A = CH$_2$, n = 10) | 10 | 9.5 ± 4.5 | 17 ± 6 | 1.8 |
| (A = CH$_2$, n = 11) | 11 | 24 ± 8 | 74 ± 11 | 3.1 |
| (A = CH$_2$, n = 12) | 12 | 42 ± 20 | 100 ± 55 | 2.4 |
| Rivastigmine | | 5500 ± 1500 | 1600 ± 30 | 0.29 |
| (−)-meptazinol | | 41000 ± 14000 | 15000 ± 4000 | 0.37 |

The related bivalent (−)-meptazinol compounds (A=CH$_2$, n=8~10) and their salts were tested for inhibition of AChE-induced Aβ aggregation.

Method

Aliquots of 2 μL Aβ (1-40) peptide (Biosource), lyophilized from 2 mg/mL HFIP solution and dissolved in DMSO, were incubated for 48 h at room temperature in 0.215 M sodium phosphate buffer (pH 8.0) at a concentration of 230 μM. For coincubation experiments, aliquots (16 μL) of human recombinant AChE (Sigma-Aldrich) (final concentration of 2.3 μM) and AChE in the presence of 2 μL of the tested inhibitors were added. Each assay was run in duplicate. To quantify amyloid fibril formation, the thioflavin T fluorescence method was then applied.

After incubation, the samples containing Aβ, Aβ plus AChE, or Aβ plus AChE in the presence of inhibitors were diluted with 50 mM glycine-NaOH buffer (pH 8.5) containing 1.5 μM thioflavin T (Sigma-Aldrich) to a final volume of 2.0 mL. Fluorescence was monitored with excitation at 446 nm and emission at 490 nm. The percent inhibition of the AChE-induced aggregation due to the presence of increasing concentrations of the inhibitor was calculated by the following expression: 100−(IFi/IFo×100), where IFi and IFo were the fluorescence intensities obtained for Aβ plus AChE in the presence and in the absence of inhibitor, respectively, after subtracting the fluorescence of respective blanks. Inhibition curves and linear regression parameters were obtained for each compound, and the $IC_{50}$ was extrapolated.

Results for Aβ Aggregation Inhibition Tests

The bivalent (−)-meptazinol compounds (wherein A is $CH_2$ and n is 9 or 10) markedly prevented the AChE-induced Aβ aggregation with $IC_{50}$ values of 79 μM and 83 μM, nearly 2 times that of propidium ($IC_{50}$ 159 μM).

Table 2 shows the inhibition of AChE-induced Aβ aggregation by bivalent (−)-meptazinol compounds (A=$CH_2$, n=8~10).

TABLE 2

| Compounds | linker length (n) | Inhibition (%) 100 μM ± SEM | Inhibition (%) 400 μM ± SEM | $IC_{50}$ ± SEM (μM) |
|---|---|---|---|---|
| Propidium iodine | | 16.7 ± 4.4 | 79.2 ± 5.9 | 158.6 ± 1.4 |
| (−)-MEP | | nd* | 0 | nd* |
| (A = $CH_2$, n = 8) | 8 | 0 | 0.15 ± 0.2 | nd* |
| (A = $CH_2$, n = 9) | 9 | 74.4 ± 4.3 | 91.7 ± 3.6 | 79.4 ± 1.4 |
| (A = $CH_2$, n = 10) | 10 | 66.6 ± 1.7 | 81.8 ± 1.2 | 83.4 ± 1.2 |

*nd: not determined.

In summary, results from cholinesterase inhibiting test and AChE-induced Aβ aggregation test demonstrated that the bivalent (−)-meptazinol compounds and/or their salts were novel bivalent inhibitors of both AChE and Aβ aggregation. They showed increased potency for the inhibition of AChE and BChE, compared with (−)-MEP hydrochloride. Among them, 5 compounds were nearly 1000 times more potent than (−)-MEP hydrochloride. The most potent bivalent (−)-meptazinol compound (wherein A is $CH_2$ and n is 9) inhibited both AChE and BChE at nM level, which was 10000 and 1500 times more potent than (−)-MEP hydrochloride, respectively. Aβ aggregation test showed that the bivalent (−)-meptazinol compounds (wherein A is $CH_2$ and n is 9 or 10) inhibited AChE-induced Aβ aggregation by a factor of 2 compared with propidium. In a word, the bivalent (−)-meptazinol compounds and/or their salts that the invention related to were novel AChE inhibitors with dual action on Aβ aggregation. They had a potential to be drug candidates with high therapeutic index and low toxicity for neurodegenerative disorders and dementias, such as AD.

FIG. 1 illustrates the correlation between mice AChE and BChE inhibitory potency (−log$IC_{50}$) and the alkylene chain length (n) in the corresponding bivalent (−)-meptazinol compounds (A=$CH_2$, n=2~12).

The following specific preparation examples further illuminated the present invention. However, they should not be construed as restricting the invention.

EXAMPLE 1

(−)-nor-MEP preparation

A stirred suspension of (−)-MEP (20.9 g, 89.70 mmol) and $KHCO_3$ (157 g, 1.57 mol) in boiling $CHCl_3$ (2 L) was treated with phenyl chloroformate (97 mL, 770 mmol) at 40° C. and refluxed for 3 hr. $H_2O$ (1 L) was added, and the $CHCl_3$ phase was separated and concentrated in vacuo to give a yellowish oil. The residue was dissolved in MeOH (1.4 L), treated with an aqueous solution (1 L) containing 138 g (1 mol) of $K_2CO_3$, and stirred under $N_2$ at room temperature for 18 h. After the MeOH was removed, the residue was neutralized with 6M HCl (270 mL), adjusting pH to 5, and extracted with $Et_2O$ (1200 mL, 800 mL). The combined $Et_2O$ extracts were dried with anhydrous $Na_2SO_4$. Evaporation of the solvent under reduced pressure gave brownish yellow oil (34 g). And the oily residue was purified by chromatography on silica gel. Eluting with $Et_2O/CHCl_3$ afforded yellowish (−)—N-Carboethoxy-nor-MEP (29 g, 95%).

The mixture of (−)—N-Carboethoxy-nor-MEP (22 g, 64.9 mmol) and 85% hydrazine hydrate (170 ml, 2.98 mol.) was refluxing for 4 h under $N_2$ atmosphere. After cooling, water (200 ml) was added and the residue was extracted with ether (600 ml, 200 ml×2). The combined $Et_2O$ extracts were dried with anhydrous $Na_2SO_4$. After filtration and evaporation, brownish yellow oil (21 g) was obtained. The oil underwent chromatography on a silica gel column and gradient elution with $EtOH/CHCl_3$ solution, affording (−)-nor-MEP (6.07 g, 43%) as whitish to yellowish oil.

$^1$HNMR (DMSO-$d_6$) 9.42 (H, s, OH), 7.16 (H, t), 6.74~6.65 (3H, m), 3.49 (H, d), 3.21 (H, d), 3.08~3.00 (2H, m), 2.14 (H, m), 1.77~1.55 (7H, m), 0.49 (3H, t)

LC-MS (ESI) 220.1 $[M+1]^+$

EXAMPLE 2

Compounds and corresponding hydrochlorides of the formula (I) (A=$CH_2$, n=2~3 and 6~12): Preparation of N,N'-(1',9'-Nonylene)-bis-(−)-nor-MEP Hydrochloride Triethylamine (1.13 mL, 8.12 mmol) and 1,9-dibromononane (0.423 mL, 2.03 mmol) were added to a solution of (−)-nor-MEP (0.89 g, 4.06 mmol) in acetonitrile (11 mL). The reaction mixture was refluxed for 2 h. Evaporation of the solvent gave a residue, which was diluted with saturated $Na_2CO_3$ solution (10 ml) and extracted with $CHCl_3$ (20 ml, 10 ml×3). The combined $CHCl_3$ extracts were dried (anhydrous $Na_2SO_4$) and evaporated under reduced pressure. The brownish residue (1.60 g) was purified by chromatography on silica gel. Eluting with EtOAc/petroleum ether (1:2) afforded the corresponding compound as a yellowish oil (0.71 g, 62.3%). Addition of dry HCl-ether (10.6 ml) to the solution of the resulting oil (0.67 g) in dry ether (20 ml) and adjusting the pH to 4 gave the final salt as white powder. After the powders were collected and dried overnight in a vacuum drier at the presence of $P_2O_5$, the hydrochloride of the corresponding compound (0.62 g, 81.9%) were finally obtained. mp.118~124° C., $[\alpha]_D$=−39.13° (c=0.32, MeOH).

$^1$HNMR (DMSO-$d_6$) 10.10 (brs, ½H, $NH^+$, $D_2O$ exchange), 9.95 (brs, ½H, $NH^+$, $D_2O$ exchange), 9.56~9.44 (m, 2H, Ar—OH, $D_2O$ exchange), 8.41 (brs,½H, $NH^+$, $D_2O$ exchange), 8.34 (brs,½H, $NH^+$, $D_2O$ exchange), 7.19~7.11 (m, 2H, Ar—H), 6.84~6.64 (m, 6H, Ar—H), 3.82 (d, H, J=14.09 Hz, N—$CH_2$), 3.53 (d, H, J=13.7 Hz, N—$CH_2$), 3.38~3.27 (m, 3H, N—$CH_2$), 3.15~3.04 (m, 7H, N—$CH_2$), 2.38~2.32 (m, H, $CH_2$), 2.10~2.01 (m, 3H, $CH_2$), 1.79~1.70 (m, 12H, $CH_2$), 1.54~1.27 (m, 14H, $CH_2$), 0.47 (t, 6H, $CH_3$)

LC-MS (ESI) $[M+1]^+$563.5; $[M+2]^{2+}$282.3

EXAMPLE 3

Compounds of the formula (I) (A=CO, n=4~5): preparation of N,N'-(1',4'-Succinyl)-bis-(−)-nor-MEP Dry triethylamine (1.84 mL, 12.23 mmol) was added to a solution of (−)-nor-MEP (1.45 g, 6.63 mmol) in dry $CH_2Cl_2$ (25 mL). Then succinyl chloride (0.382 mL, 3.30 mmol) in dry $CH_2Cl_2$ (10 mL) was added dropwise at 0° C. The mixture was stirred for 15 min at 0° C. The mixture was washed with $H_2O$ (5 mL), 2M HCl (5 mL), and then $H_2O$ (5 mL). The combined water layers were back-extracted with $CH_2Cl_2$ (10 mL×3). All the $CH_2Cl_2$ layers were combined and dried with anhydrous $Na_2SO_4$. Evaporation of the solvent under reduced pressure gave a greenish foam (1.85 g). Purification by chromatography on silica gel and gradient elution with petroleum ether/EtOAc afforded the product as a yellowish crystal (0.73 g, 41.4%). mp 117~120° C.

$^1$HNMR (DMSO-$d_6$) 8.79 (s, 2H, Ar—OH, $D_2O$ exchange), 7.19 (t, 2H, Ar—H), 6.78~6.70 (m, 6H, Ar—H), 4.88 (d, 2H, J=14.66 Hz, N—$CH_2$), 3.59 (m, 2H, $J_1$=11.73 Hz, $J_2$=6.23 Hz, N—$CH_2$), 3.08 (d, 2H, J=15.03 Hz, N—$CH_2$), 2.91 (t, 2H, J=1.73 Hz, N—$CH_2$), 2.83 (d, 2H, J=13.56 Hz, N—$CH_2$), 2.39 (dm, 2H, J=7.7 Hz, $CH_2$), 2.33 (d, 2H, J=13.2 Hz, N—$CH_2$), 1.82~1.48 (m, 14H, $CH_2$), 0.68 (t, 6H, J=7.33 Hz, $CH_3$)

LC-MS (ESI) [M+1]$^+$521.3

EXAMPLE 4

Compounds and corresponding hydrochlorides of the formula (I) (A=$CH_2$, n=4~5): preparation of N,N'-(1',4'-Butylene)-bis-(−)-nor-MEP Hydrochloride A solution of N,N'-(1',4'-succinyl)-bis-(−)-nor-MEP (0.56 g, 1.08 mmol) in dry THF (15 ml) was added dropwise to lithium aluminum hydride (0.20 g, 5.26 mmol) in dry THF (15 ml) in cooling water bath. The mixture was refluxed for 1 h, and then $H_2O$ (0.28 mL), 15% NaOH (0.28 mL), and $H_2O$ (0.84 mL) were added and the mixture was stirred and then filtered. The combined THF solution was evaporated to remove solvents. The residue was treated with $H_2O$ (15 mL) and $CHCl_3$ (30 mL). Drops of 10% $NH_4C$ (1.5 mL) were added to adjust the pH to 9, and the residue was extracted with $CHCl_3$ (10 mL×4). The combined $CHCl_3$ was dried with anhydrous $Na_2SO_4$ and concentrated in vacuo to give a orange oil residue (0.55 g), which was chromatographed on silica gel eluted with MeOH/$CHCl_3$ to provide the corresponding product (0.19 g, 35.8%) as an orange oil.

Addition of dry HCl-ether (2.2 ml) to the solution of the resulting oil (0.19 g) in dry ether (20 ml) gave the final salt as white powder. After the powders were collected and dried overnight in a vacuum drier at the presence of $P_2O_5$, the hydrochloride of the corresponding compound (0.12 g, 55%) were finally obtained. mp. 110~115° C., $[\alpha]_D$=−51.96° (c 0.092, MeOH).

$^1$HNMR (DMSO-$d_6$) 9.98 (brs,½H, NH$^+$, $D_2O$ exchange), 9.77 (brs,½H, NH$^+$, $D_2O$ exchange), 9.56-9.43 (m, 2H, Ar—OH, $D_2O$ exchange), 8.46 (brs, 1H, NH$^+$, $D_2O$ exchange), 7.21-7.13 (m, 2H, Ar—H), 6.85-6.65 (m, 6H, Ar—H), 3.83 (t, H, J=13.3 Hz, N—$CH_2$), 3.52 (t, H, J=13.7, N—$CH_2$), 3.36-3.15 (m, 10H, N—$CH_2$), 2.38 (m, H, $CH_2$), 2.10-1.46 (m, 19H, $CH_2$), 0.49 (t, 6H, $CH_3$)

LC-MS (ESI) [M+1]$^+$493.3 [M+2]$^{2+}$247.2

What is claimed is:

1. Bivalent (−)-meptazinol derivatives and/or their salts of the following formula:

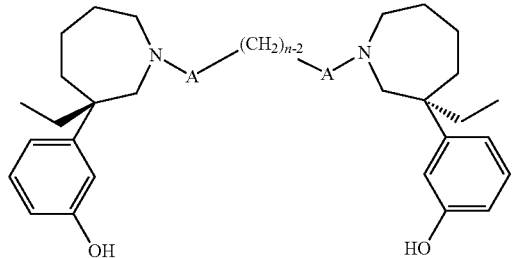

wherein A is C=O or $CH_2$ and wherein when A is C=O, n is an integer from 2 to 12 and when A is $CH_2$, n is an integer of 8, 9, 10 11, and 12.

2. The bivalent (−)-meptazinol derivatives and/or their salts according to claim 1, wherein A is C=O.

3. The bivalent (−)-meptazinol derivatives and/or their salts according to claim 1, wherein A is $CH_2$.

4. A bivalent (−)-meptazinol derivative and/or its salts according to claim 3, wherein A is $CH_2$ and n is 9.

5. A method for preparing the bivalent (−)-meptazinol derivatives and/or their salts according to claim 2, wherein two (−)-nor-MEPs are connected by acylation using α,ω-alkanediacyl dihalides.

6. A method for preparing the bivalent (−)-meptazinol derivatives and/or their salts according to claim 3, wherein two (−)-nor-MEPs are connected by alkylation using α,ω-dihaloalkanes.

7. A method for preparing the bivalent (−)-meptazinol derivatives and/or their salts according to claim 3, wherein compounds of the following formula

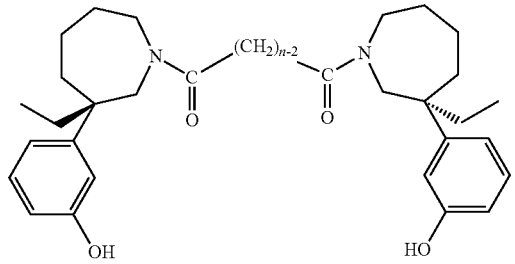

are reduced by lithium aluminum hydride, where n is an integer of 8, 9, 10, 11 and 12.

8. The bivalent (−)-meptazinol derivatives and/or their salts according to claim 1, wherein said salts are pharmaceutical acceptable acid addition salts of the bivalent (−)-meptazinol derivatives formed with pharmaceutically acceptable inorganic and organic acids.

9. The bivalent (−)-meptazinol derivatives and/or their salts according to claim 1, wherein said salts are pharmaceutically acceptable base addition salts of the bivalent (−)-meptazinol derivatives formed with pharmaceutical acceptable bases.

10. The bivalent (−)-meptazinol derivatives and/or their salts according to claim 8, wherein said pharmaceutically acceptable inorganic acids are hydrochloric acid, hydrobromic acid, hydroiodic acid, sulfuric acid, phosphoric acid, or any mixture of the above acids, and wherein said pharmaceutically acceptable organic acids are tartaric acid, acetic acid, maleic acid, fumaric acid, benzoic acid, succinic acid, lactic acid, citric acid, gluconic acid, methanesulfonic acid, phenylsulfonic acid, p-toluenesulfonic acid, or any mixture of the above acids.

11. The bivalent (−)-meptazinol derivatives and/or their salts according to claim 9, wherein said pharmaceutically acceptable bases are bases contain potassium, sodium, lithium, magnesium, calcium, or any mixture of the metal ion bases.

12. A method of treating neurodegenerative disorders and dementias, which comprises administering an effective amount of the bivalent (−)-meptazinol derivatives and/or their salts as defined in claim 1.

13. The method of claim 12, wherein the neurodegenerative disorder is Alzheimer's Disease (AD) or Parkinson's Disease (PD), wherein the dementia is senile dementia (Alzheimer's Disease, AD), dementia with Lewy bodies (DLB), or vascular dementia (VaD).

14. The bivalent (−)-meptazinol derivatives and/or their salts according to claim 3, wherein said salts are pharmaceutical acceptable acid addition salts of the bivalent (−)-meptazinol derivatives formed with pharmaceutically acceptable inorganic and organic acids.

15. The bivalent (−)-meptazinol derivatives and/or their salts according to claim 4, wherein said salts are pharmaceutical acceptable acid addition salts of the bivalent (−)-meptazinol derivatives formed with pharmaceutically acceptable inorganic and organic acids.

16. The bivalent (−)-meptazinol derivatives and/or their salts according to claim 2, wherein said salts are pharmaceutically acceptable base addition salts of the bivalent (−)-meptazinol derivatives formed with pharmaceutical acceptable bases.

17. The bivalent (−)-meptazinol derivatives and/or their salts according to claim 3, wherein said salts are pharmaceutically acceptable base addition salts of the bivalent (−)-meptazinol derivatives formed with pharmaceutical acceptable bases.

18. The bivalent (−)-meptazinol derivatives and/or their salts according to claim 4, wherein said salts are pharmaceutically acceptable base addition salts of the bivalent (−)-meptazinol derivatives formed with pharmaceutical acceptable bases.

19. The bivalent (−)-meptazinol derivatives and/or their salts according to claim 16, wherein said pharmaceutically acceptable bases are bases contain potassium, sodium, lithium, magnesium, calcium, or any mixture of the metal ion bases.

20. The bivalent (−)-meptazinol derivatives and/or their salts according to claim 17, wherein said pharmaceutically acceptable bases are bases contain potassium, sodium, lithium, magnesium, calcium, or any mixture of the metal ion bases.

21. The bivalent (−)-meptazinol derivatives and/or their salts according to claim 18, wherein said pharmaceutically acceptable bases are bases contain potassium, sodium, lithium, magnesium, calcium, or any mixture of the metal ion bases.

22. The bivalent (−)-meptazinol derivatives and/or their salts according to claim 14, wherein said pharmaceutically acceptable inorganic acids are hydrochloric acid, hydrobromic acid, hydroiodic acid, sulfuric acid, phosphoric acid, or any mixture of the above acids, and wherein said pharmaceutically acceptable organic acids are tartaric acid, acetic acid, maleic acid, fumaric acid, benzoic acid, succinic acid, lactic acid, citric acid, gluconic acid, methanesulfonic acid, phenylsulfonic acid, p-toluenesulfonic acid, or any mixture of the above acids.

23. The bivalent (−)-meptazinol derivatives and/or their salts according to claim 15, wherein said pharmaceutically acceptable inorganic acids are hydrochloric acid, hydrobromic acid, hydroiodic acid, sulfuric acid, phosphoric acid, or any mixture of the above acids, and wherein said pharmaceutically acceptable organic acids are tartaric acid, acetic acid, maleic acid, fumaric acid, benzoic acid, succinic acid, lactic acid, citric acid, gluconic acid, methanesulfonic acid, phenylsulfonic acid, p-toluenesulfonic acid, or any mixture of the above acids.

* * * * *

UNITED STATES PATENT AND TRADEMARK OFFICE
CERTIFICATE OF CORRECTION

PATENT NO.         : 8,232,270 B2
APPLICATION NO.    : 12/309580
DATED              : July 31, 2012
INVENTOR(S)        : Zhuibai Qiu et al.

It is certified that error appears in the above-identified patent and that said Letters Patent is hereby corrected as shown below:

On the Title page of the patent, item (54), and in the Specification, column 1 at line 3, in the title, please correct the last word of the title from "FUTILIZATION" to --UTILIZATION--.

Signed and Sealed this
Fourth Day of June, 2013

Teresa Stanek Rea
*Acting Director of the United States Patent and Trademark Office*